United States Patent [19]

de Graaf et al.

[11] 4,308,413
[45] Dec. 29, 1981

[54] PROCESS FOR THE PREPARATION OF ALKYLBENZENES

[75] Inventors: Theodorus F. M. de Graaf, Beek; Ludovicus H. W. Janssen, Geleen, both of Netherlands

[73] Assignee: Stamicarbon, B.V., Geleen, Netherlands

[21] Appl. No.: 166,298

[22] Filed: Jul. 7, 1980

[30] Foreign Application Priority Data

Jul. 7, 1979 [NL] Netherlands ............ 7905327

[51] Int. Cl.³ ............................. C07C 5/40
[52] U.S. Cl. .................... 585/434; 585/430
[58] Field of Search ................ 585/430, 434

[56] References Cited

U.S. PATENT DOCUMENTS 3,502,736  3/1970  Sato et al. ............... 585/434
3,856,870 12/1974  Hayes ..................... 585/434
3,903,185  9/1975  Vogel et al. ............. 585/434
4,233,244 11/1980  Patterson ................ 585/434
4,237,070 12/1980  Patterson ................ 585/434
4,243,826  1/1981  Antos ..................... 585/434

OTHER PUBLICATIONS

Castellan et al., J. Catalysis 50 (1977), pp. 172-175.

Primary Examiner—Arthur P. Demers
Attorney, Agent, or Firm—Cushman, Darby & Cushman

[57] ABSTRACT

A method for the preparation of an alkyl benzene by dehydrogenation of the corresponding alkenyl cyclohexene in the presence of carrier borne noble metal catalyst wherein a non-acidic material is used as the catalyst carrier and the reaction is initially conducted at a lower temperature for a period of time and subsequently at a higher temperature.

8 Claims, No Drawings

PROCESS FOR THE PREPARATION OF ALKYLBENZENES

The invention relates to a process for the preparation of an alkyl benzene by the dehydrogenation of the corresponding alkenyl cyclohexene in the presence of a carrier-borne noble metal catalyst.

BACKGROUND OF THE INVENTION

A similar process is described in Russian Patent Specification No. 236,462. In the process therein described, vinyl cyclohexene is converted at a temperature of 300°-400° C. to ethyl benzene in the presence of a catalyst consisting of palladium or carbon with a conversion of 95% and a selectivity of 92% towards ethyl benzene. Another similar process is described in the Journal of Catalysis 50 (1977) p. 172. That process employs palladium-on-alumina catalyst with the vinyl cyclohexene being completely converted to ethyl benzene. One significant disadvantage of these processes is that the catalyst activity decreases fairly rapidly with the catalyst being practically fully deactivated after about 1-2 weeks.

The present invention however, overcomes this disadvantage by providing a process by which an alkenyl cyclohexene can be converted substantially quantitatively to the corresponding alkyl benzene with the aid of a catalyst, which even after several months of operation exhibits very little deterioration in activity.

DESCRIPTION OF THE INVENTION

According to the present invention, this is achieved by using a non-acidic material as the catalyst carrier and by conducting the reaction first for a minimum of 1 hour at a temperature of between about 200° and about 275° C. and subsequently at a temperature of between about 275° and about 450° C.

The dehydrogenation according to the present invention is performed in the presence of a noble metal catalyst. As such, platinum, palladium, ruthenium or iridium may, for example, be used. Palladium is preferably used as the catalytically active material, as a result of the surprising discovery that with palladium the alkenyl cyclohexene is converted with a very high selectivity towards alkyl benzene.

According to the present invention, the noble metal catalyst is applied on a non-acidic carrier. This is because of the remarkable finding that when an acidic carrier material such as alumina is used, while the catalyst has a high initial activity, this activity then very rapidly decreases. However, with a non-acidic carrier the activity of the catalyst is retained.

As the non-acidic carrier material, basic substances such as oxides, hydroxides or carbonates of calcium and/or magnesium, or barium sulphate may be used, but neutral carrier materials such as carbon or neutral silicon oxide may also be used. By preference magnesium oxide is used as the carrier material.

The quantity of catalyst per quantity of alkenyl cyclohexene to be converted by the process according to the present invention can vary within wide limits. For example, varying quantities may be employed so that the space velocity, expressed as liters liquid alkenyl cyclohexene per liter catalyst per hour will range from about 0.01 to about 500. Space velocities of between about 0.5 and about 50 are preferably chosen. The quantity of catalycically active noble metal in the catalyst can also be varied within wide limits, for example from about 0.01 to about 10 wt.% noble metal, calaculated relative to the total catalyst weight. The quantity of noble metal in the catalyst is preferably from about 0.4 to about 4 wt.%, calculated relative to the total catalyst weight. A catalyst composition of from about 0.5 to about 3 wt.% palladium on magnesium oxide as carrier material has been found to be especially suitable.

In the process according to the present invention the noble metal catalyst retains its high initial activity for a substantial period of time. It has, moreover, been found that when the activity eventually decreases, the catalyst can be regenerated by simply passing air or other gases containing oxygen over the catalyst. In this manner the original activity can be restored.

According to the present invention, the alkenyl cyclohexene is first passed over the catalyst for a minimum of 1 hour at a relatively low temperature of between about 200° and about 275° C. and then at a temperature of between about 275° and about 450° C. The initial contacting at the lower temperature is done because it has been found that the catalyst is deactivated very rapidly if the alkenyl chclohexene is brought immediately into contact with the catalyst at the higher temperature. Preferably the alkenyl cyclohexene is initially passed over the catalyst for a minimum of 8 hours, more preferably a minimum of 24 hours, at a temperature of between about 200° and about 275° C. and then at a temperature of between about 275° and about 450° C. The temperature preferably applied are about 225° to 260° C. for the initial operation at the lower temperature and about 300° to about 350° C. for the subsequent operation at the higher temperature.

The process according to the present invention is preferably performed at atmospheric pressure. Application of elevated pressure is feasible, but does not provide any additional advantages. Moreover, the dehydrogenation equilibrium is adversely affected by applying higher pressures.

In the process according to the present invention various alkenyl cyclohexenes can be used as the starting material. For example, vinyl cyclohexene, isopropenyl cyclohexene, and alkyl-substituted derivatives of these can be used as the starting material. These substances can be obtained by dimerization and codimerization of conjugated diolefins. For example, vinyl cyclohexene can be obtained by dimerization of butadiene; isopropenyl cyclohexene by codimerization of butadiene of isoprene; and methyl isopropenyl cyclohexene by dimerization of isoprene.

It has been discovered that the presence of peroxides in the alkenyl cyclohexene to be converted adversely affects catalyst life during conversion. An alkyl cyclohexene containing less than 5 ppm peroxides is, therefore, preferably used as the starting material. An alkenyl cyclohexene that is substantially free of peroxides can be prepared by purifying technical grade alkenyl cyclohexene of peroxides and storing it in an environment substantially free of oxygen. Peroxides can be removed from alkenyl cyclohexene by several methods including, for example, by selective hydrogenation; dissociation by heating; or distillation over a reducing agent such as triphenyl phosphine.

Although, the reaction of the present invention can in principle be carried out in the liquid phase, preference is given to carrying out the reaction in the gas phase. This reaction is preferably carried out in the presence of an inert gas, such as for example, nitrogen. The presence of an inert gas in the reaction mixture has the additional advantage of favoring the reaction equilibrium.

In principle, hydrogen can also be included in the reaction mixture, but the formation of hydrogenated by-products such as alkyl cyclohexane then increases. The reaction is, thererfore, preferably carried out without hydrogen being added. In the process according to the present invention, the hydrogen liberated during dehydrogenation has little, if any, influence on the selectivity towards alkyl benzene.

In the process according to the present invention, the alkenyl cyclohexene added is almost completely converted to a product that consists substantially quantitatively, i.e., 99.5% and higher, of alkyl benzene. This product can be separated by, for example, cooling from the resultant reaction mixture, which also contains a quantity of hydrogen and in some cases nitrogen in addition to reaction product. The separated product can be directly applied, without further treatment, for further conversions. The dehydrogenation product of vinyl cyclohexene, for instance, which consists substantially quantitatively of ethyl benzene, can thus be directly converted to styrene. The dehydrogenation product of isopropenyl cyclohexene, viz. isopropyl benzene, can be applied as the starting material for the preparation of α-methyl styrene, or be converted to phenol by oxidation. In the same manner, methyl isopropyl benzene, obtained from methyl isopropenyl cyclohexene can be used in the preparation of inter alia, methyl phenol.

The invention is further elucidated but not limited by the following example and comparative examples.

EXAMPLES

EXAMPLE 1

In an electrically heated glass tubular reactor with a diameter of 20 mm and a length of 50 cm, provided with a thermocouple tube, a 10 cm³ catalyst bed was introduced, consisting of 3 wt.% palladium on magensium oxide.

With complete exclusion of oxygen, a gas mixture of vinyl cyclohexene and nitrogen was fed to the catalyst in a ratio of 1:1 by volume, which mixture had been obtained by evaporating liquid vinyl cyclohexene while introducing oxygen free nitrogen. The vinyl cyclohexene had been previously distilled over triphenyl phosphine to remove peroxides, such that peroxides were not longer analytically demonstrable in the distilled product (>2 ppm). The gas mixture throughput rate was 1 volume liquid vinyl cyclohexene per volume catalyst per hour. The temperature in the reactor was maintained at 250° C.

Downstream of the reactor a cooler was installed, in which the gaseous reaction mixture formed was condensed. The composition of the condensed product was periodically analyzed, and the results are given in the table below.

After 600 hours the reactor temperature was increased to 325° C. and the volume ratio of vinyl cyclohexene to nitrogen also modified to 1:3. The gaseous reaction mixture was condensed and analyzed in the same way. The results are again given in the table below. The test was discontinued after a total of 1200 hours of operation.

| Hours of Operation | Ethyl benzene content of condensate (in %) | Remarks |
| --- | --- | --- |
| 26 | 90 | |
| 100 | 90 | |
| 200 | 90 | |
| 314 | 89 | |
| 408 | 89 | The remainder of the |
| 500 | 87 | condensate consisted |
| 600 | 87 | substantially in toto |
| 700 | 99.6 | of ethyl cyclohexane |
| 792 | 99.5 | |
| 911 | 99.5 | |
| 1009 | 99.5 | |
| 1140 | 99.5 | |
| 1200 | 99.5 | |

Thus, it is clearly demonstrated that even after 1200 hours of operation the catalyst retains its activity.

EXAMPLE 2 (comparative example)

In the same way as in Example 1, an identical gas mixture of vinyl cyclohexene and nitrogen was passed through the reactor, which contained palladium on alumina (0.5 wt.% Pd) as catalyst. The reaction temperature was maintained at 250° C. for 214 hours and subsequently increased to 325° C. The gaseous reaction mixture was condensed and analayzed in the same way. The results are given in the table below.

| Hours of operation | Ethyl benzene content of condensate (in %) | Remarks |
| --- | --- | --- |
| 99 | 91 | Remainder consisted |
| 192 | 90 | mainly of ethyl cyclo- |
| 285 | 95 | hexane |
| 311 | 95 | |
| 314 | 95 | Condensate also con- |
| 334 | 85 | tained 4% unconverted vinyl cyclohexane |

Thus, it is clearly demonstrated that even after increasing the temperature the selectivity towards ethyl benzene is condsiderably lower than in Example 1. In addition, both the conversion and the selectivity towards ethyl benzene show a marked decrease within a relatively short time (120 hours after temperature increase).

EXAMPLE 3 (comparative example)

By the same method as in Example 1, an identical gas mixture of vinyl cyclohexene and nitrogen was passed through the reactor, which contained the same catalyst as in Example 1. The reaction temperature was 300° C. The gaseous reaction mixture was condensed and analyzed in the same way. The results are given in the table below.

| Hours of operation | Ethyl benzene content of condensate (in %) | Unconverted vinyl cyclohexene (in %) |
| --- | --- | --- |
| 28 | 97 | — |
| 77 | 97 | — |
| 100 | 96 | — |
| 116 | 94 | 0.3 |
| 142 | 85 | 3.5 |

Thus, it is clearly demonstrated that the selectivity towards ethyl benzene is lower than in Example 1. In addition, the catalyst activity decreases sharply after a relatively short time (116 hours), as regards both conversion and selectivity.

What is claimed is:

1. Process for the preparation of an alkyl benzene by dehydrogenation of the corresponding alkenyl cyclohexene in the presence of a carrier borne noble metal catalyst wherein a non-acidic material is used as the catalyst carrier, and the reaction is initially conducted for a minimum of about 1 hour at a temperature between about 200° C. and about 275° C. and subsequently at a temperature between about 275° C. and about 450° C.

2. Process in accordance with claim 1, wherein the reaction is initially conducted for a minimum of about 8 hours at a temperature between about 200° C. and 275° C. and subsequently at a temperature between about 275° C. and 450° C.

3. Process in accordance with claim 1, wherein the reaction is initially conducted for a minimum of about 24 hours at a temperature between about 200° C. and about 275° C. and subsequently at a temperature between about 275° C. and 450° C.

4. Process in accordance with claim 1, wherein the reaction is initially conducted at a temperature between about 220° C. and about 260° C. and subsequently between about 300° and about 350° C.

5. Process in accordance with claim 1, wherein the catalyst carrier is magnesium oxide.

6. Process in accordance with claim 1, wherein the reaction is conducted in the presence of a maximum of 5 ppm peroxide, calculated relative to the quantity by weight of alkyl cyclohexene.

7. Process in accordance with claim 1, wherein the reaction is conducted in the gaseous phase in the presence of an inert gas.

8. Process in accordance with claim 7, wherein the reaction is conducted at atmospheric pressure.

* * * * *